United States Patent
Goldowsky

(10) Patent No.: US 6,290,640 B1
(45) Date of Patent: Sep. 18, 2001

(54) UNCOUPLED ROTARY LINEAR PUMP

(75) Inventor: Michael Philip Goldowsky, Valhalla, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/432,896

(22) Filed: Nov. 2, 1999

(51) Int. Cl.[7] ........................................ A61M 1/10
(52) U.S. Cl. ................................................ 600/16
(58) Field of Search ........................... 600/16, 17

(56) References Cited

U.S. PATENT DOCUMENTS

| | | |
|---|---|---|
| 4,210,409 | 7/1980 | Child . |
| 4,375,941 | 3/1983 | Child . |
| 4,675,563 | 6/1987 | Goldowsky . |
| 5,360,445 | 11/1994 | Goldowsky . |
| 5,676,651 | 10/1997 | Larson, Jr. et al. . |
| 5,924,975 | 7/1999 | Goldowsky . |

*Primary Examiner*—Scott M. Getzow
(74) *Attorney, Agent, or Firm*—Francis L. Conte

(57) ABSTRACT

A fluid pump includes a piston mounted in a housing. A check valve is disposed in the piston for controlling fluid flow. A linear motor joins the piston and housing for axial oscillation of the piston to pump the fluid in unidirectional flow. A rotary motor includes magnet strips mounted in the piston and a cooperating rotary drive coil mounted in the housing. The rotary motor is magnetically uncoupled from the linear motor.

17 Claims, 2 Drawing Sheets

UNCOUPLED ROTARY LINEAR PUMP

BACKGROUND OF THE INVENTION

The present invention relates generally to pumps, and, more specifically, to blood pumps.

U.S. Pat. No. 5,924,975 discloses a linear pump which is implantable as a left ventricular assist device (LVAD) that assists a damaged heart in pumping blood. This pump includes a tubular piston disposed coaxially inside a tubular housing. Check valves are joined to the housing and piston for effecting unidirectional fluid flow as the piston reciprocates in the housing.

The piston is driven by a linear motor that includes axial drive coils mounted inside the housing which cooperate with a pair of magnet rings mounted in opposite ends of the piston. A magnetic circuit is thusly formed between the piston and housing, and the coils are commutated to control axial oscillation of the piston and resulting pumping therefrom.

The piston includes a cylindrical outer surface or journal which is spaced radially inwardly from the housing bore to define a hydrodynamic bearing having a radial gap which receives a portion of the blood being pumped. The surfaces of the piston end housing bore are smooth and define a nominally circular annulus in which the journal bearing is effected.

In a preferred embodiment, the piston rotates in addition to axially oscillating for developing hydrodynamic pressure in the blood for supporting the piston and preventing contact with the housing to prevent blood damage. The piston may be rotated by various methods which vary in complexity and efficiency.

For example, the two magnet rings used in the axial motor may be modified for use also in a rotary motor. The rings may be configured to have circumferentially spaced apart zones of different magnetic field flux density which effectively form unidirectional magnetic poles around the piston. The magnet rings are thusly effective for magnetically cooperating with the axial drive coils for axial oscillation, while also being effective for magnetically cooperating with a rotary drive coil for spinning the piston during operation.

However, this integrated axial and rotary motor configuration compromises performance of the axial motor and the rotary motor, and has correspondingly reduced efficiency. In an exemplary configuration for use in a LVAD pump, the resulting inefficiency of the motor requires about 5 watts of rotary power for developing a suitable hydrodynamic bearing. Since the rotary poles formed in the magnet rings reduce the average radial magnetic field therefrom, power for the linear motor must correspondingly increase from about 6 watts to about 7 watts in a practical example.

Motor efficiency is a significant factor in blood pump design because it affects pump size and power requirements. The pump should be as small as practical for being implanted in a living body, and should have minimum power consumption for reducing battery requirements.

Accordingly, it is desired to provide an improved linear pump having a new combination of linear and rotary motors.

BRIEF SUMMARY OF THE INVENTION

A fluid pump includes a piston mounted in a housing. A check valve is disposed in the piston for controlling fluid flow. A linear motor joins the piston and housing for axial oscillation of the piston to pump the fluid in unidirectional flow. A rotary motor includes magnet strips mounted in the piston and a cooperating rotary drive coil mounted in the housing. The rotary motor is magnetically uncoupled from the linear motor.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
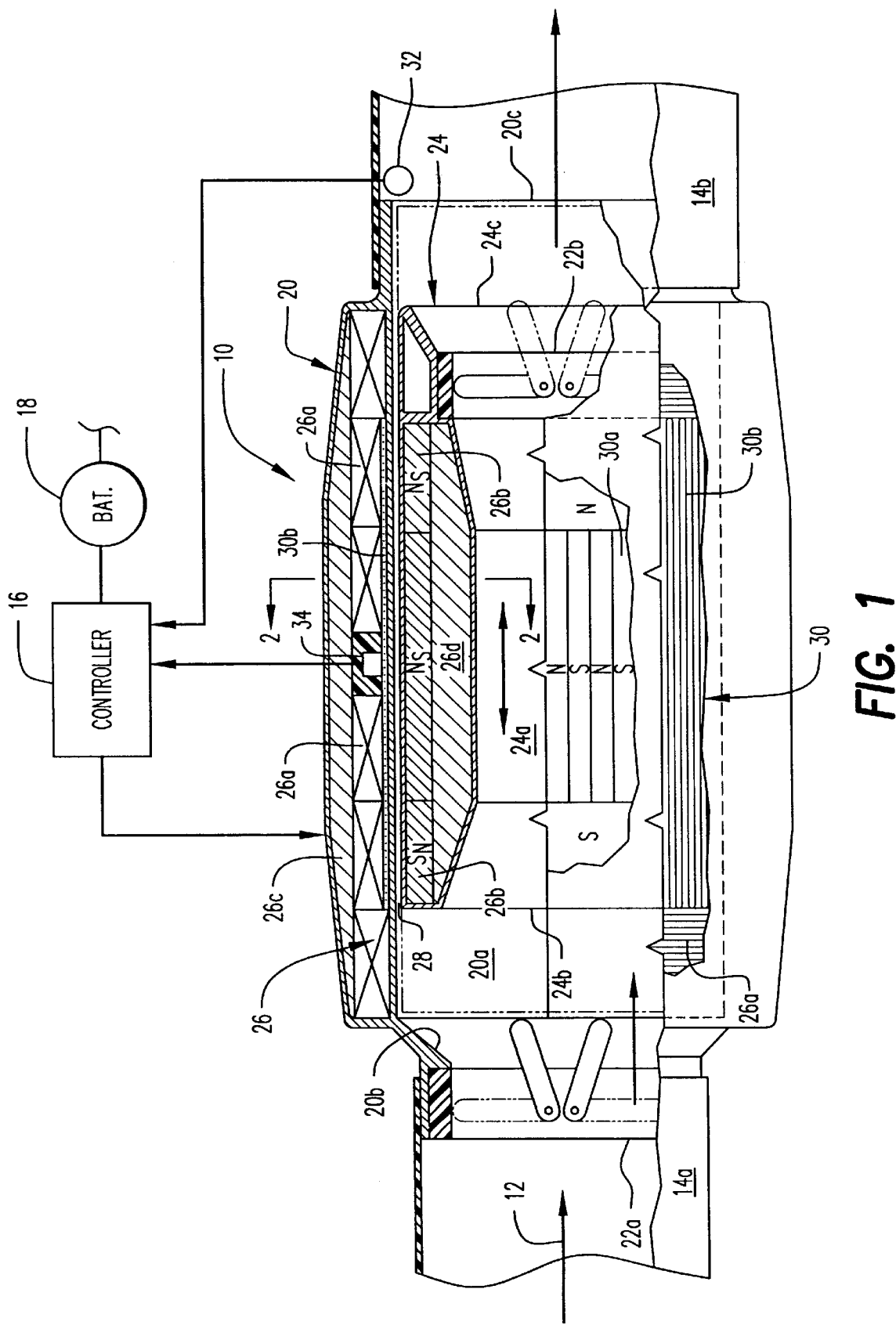
FIG. 1 is a partly sectional, side elevational view of an exemplary linear pump having axial and rotary motors in accordance with an exemplary embodiment of the present invention.

Illustrated in FIG. 1 is a linear pump 10 configured in accordance with an exemplary embodiment of the present invention for being implanted in a living body for pumping fluid or blood 12. For example, the pump is configured as a left ventricular assist device (LVAD) surgically attached between the left atrium and descending aorta of a human heart. The pump includes a suitable inlet tube 14a sutured to an opening in the left atrium, and a suitable outlet tube 14b sutured to the descending aorta.

The pump is controlled by an electrical controller 16 suitably electrically joined thereto, and is powered by an implanted battery 18 electrically joined to the controller.

The pump includes a hollow housing 20 having a coaxial, smooth cylindrical center bore 20a disposed in flow communication between a housing inlet 20b and outlet 20c axially spaced apart from each other at opposite ends of the housing.

A first, one-way check valve 22a is joined to the housing inlet for controlling flow of the blood through the housing bore. The first valve 22a may instead be located in the housing outlet if desired.

A cylindrical, hollow piston 24 is disposed coaxially in the housing bore for axial translation therein. The piston includes a coaxial, smooth center bore 24a disposed in flow communication between a piston inlet 24b and outlet 24c axially spaced apart from each other at opposite ends of the piston.

A second, one-way check valve 22b is fixedly joined in the piston outlet for controlling flow of the blood through the piston bore. The second valve may instead be installed in the piston inlet if desired.

A linear motor 26 is operatively joined in the housing and piston for axially oscillating the piston in the housing to pump the blood in unidirectional flow therethrough. The linear motor includes a plurality of axially adjoining, coaxial stator drive coils 26a mounted inside the housing. A pair of axially spaced apart permanent magnet rings 26b are mounted inside the piston at opposite axial ends thereof for magnetically cooperating with the axial drive coils to axially oscillate the piston for cyclically pumping the blood in turn through the housing and piston inlets and outlets in unidirectional flow through the housing and piston bores.

The linear motor also includes a radially outer iron core 26c mounted inside the housing and surrounding the axial drive coils 26a. A radially inner iron core 26d is mounted inside the piston radially inwardly or inboard of the magnet rings 26b. The two cores 26c,d include high-saturation magnetic iron in a suitable alloy for providing a closed loop magnetic flux path or circuit.

The two magnet rings 26b are magnetized radially oppositely from each other, and the radial flux therefrom travels through corresponding axial drive coils 26a and axially through the outer core 26c. The magnetic flux also passes axially through the inner core 26d to complete the closed magnetic circuit. As the axial drive coils 26a are energized in turn, magnetic force propels the piston axially inside the housing in the manner of a voice coil linear motor.

Since the pump is specifically configured in this exemplary embodiment for pumping blood in a living body, the housing and piston are preferably encapsulated in a suitable biocompatible material for being implanted into the body and pumping blood therethrough. This may be effected by forming the outer exposed surfaces of the housing and piston in the form of suitably thin titanium shells or cans, which themselves may be suitably coated with a biocompatible material such as carbon if desired.

The piston 24 preferably includes a cylindrical outer surface or journal which is predeterminedly spaced radially inwardly from the housing bore to define a hydrodynamic bearing therewith having a radial gap 28 for receiving a portion of the blood from the housing bore as bearing fluid for hydrodynamically supporting the oscillatory piston in the housing. The housing inner surface defining the bore is suitably smooth, and the complementary piston journal is also smooth. The piston gap 28 is nominally a circular annulus which extends completely between the opposite ends of the piston in flow communication with the housing bore.

In operation, the linear motor 26 is powered for magnetically axially translating the piston in the housing bore in a forward or eject stroke followed in turn by an aft or reset stroke. The piston axially reciprocates forward and aft to linearly pump the blood in unidirectional forward flow. The check valves 22a,b cooperate with the reciprocating piston for obtaining the unidirectional flow.

The piston is entirely bathed in the blood and provides pumping action through its bore. Blood flow through the piston gap effects a hydrodynamic bearing for suspending the piston away from the housing bore for providing substantially frictionless movement thereof, and preventing damage to the blood. By spinning the piston as it axially oscillates, substantial hydrodynamic pressure may be generated in the journal bearing.

Figure 2:
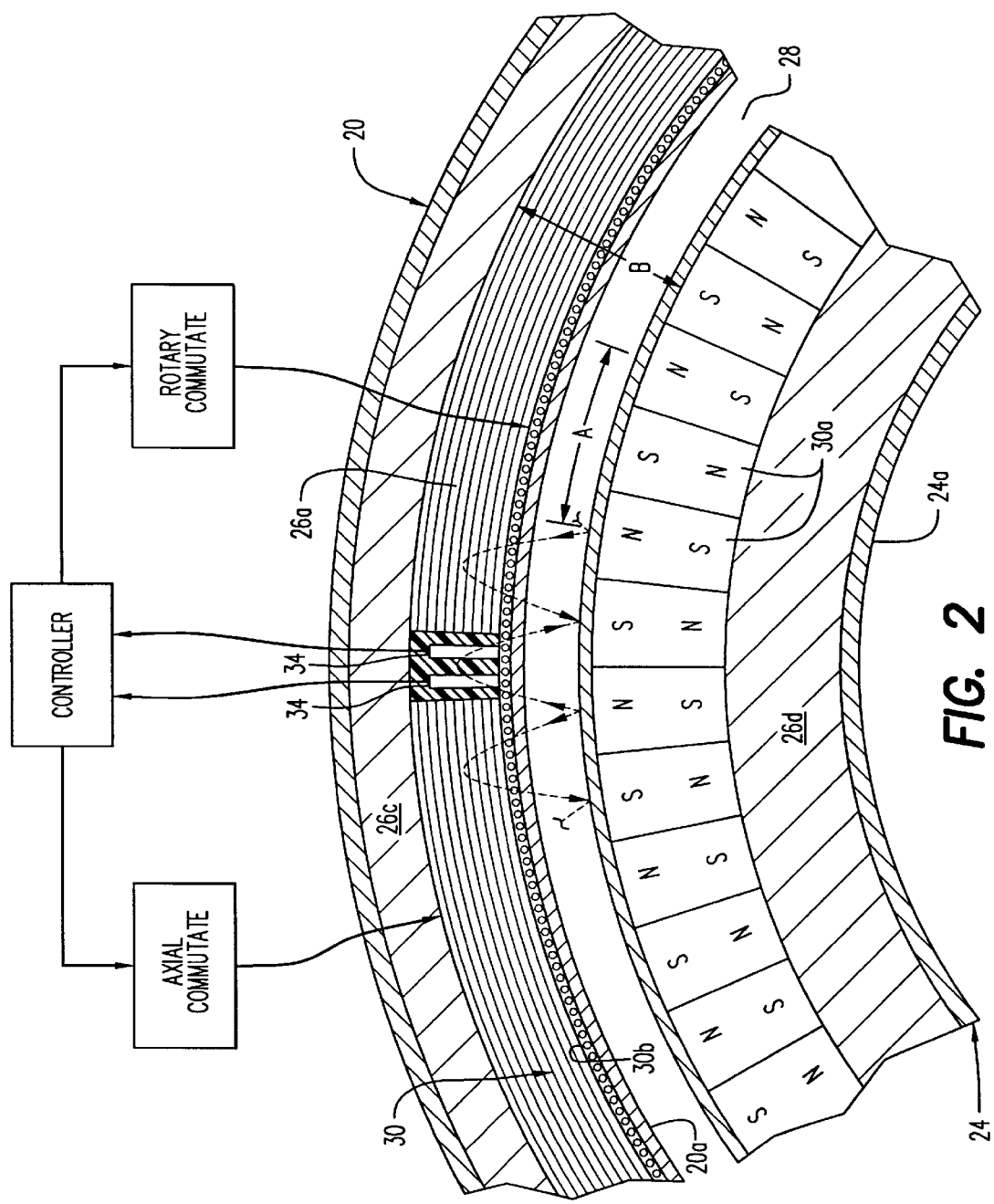
FIG. 2 is a radial sectional view through a portion of the pump illustrated in FIG. 2 and taken along line 2—2.

In accordance with the present invention, a rotary motor 30 is provided for spinning the piston independently of the linear motor for maximizing efficiency of both motors without undesirable magnetic cooperation therebetween. As shown in FIGS. 1 and 2, the rotary motor includes a plurality of circumferentially adjoining permanent magnet strips 30a fixedly mounted around the perimeter of the piston axially centrally between the opposite ends thereof. The magnet strips extend axially along the piston, with the two magnet rings 26b being mounted at opposite axial ends of the strips. The inner core 26d is disposed inboard of the magnet strips 30a and the magnet rings 26b.

The rotary motor further includes a rotary drive coil 30b mounted inside the housing around the housing bore. The axial drive coils 26a surround the rotary drive coil 30b, with the rotary drive coil being axially centrally mounted relative to both the axial drive coils and the magnet rings and strips 26b,30a.

In this configuration, the rotary motor 30 is independent and distinct from the linear motor 26, and magnetically uncoupled therefrom for independent operation to maximize efficiency thereof. For example, the 5 watts of power previously required for rotating the piston may be substantially reduced to about 0.3 watts using the independent rotary motor. And, the efficiency of the linear motor may be correspondingly increased so that the 7 watts of power previously required for axial reciprocation may be reduced to about 6 watts. This is a substantial reduction in power requirement for the linear pump in a typical LVAD application which may be used to advantage as desired.

In the exemplary embodiment illustrated in FIG. 1, two groups of three axial drive coils 26a are used to produce axial motion of the piston. The axial drive coils are wound circumferentially around the housing to cooperate magnetically with the magnetic poles of the magnet rings 26b to provide axially directed force for reciprocating the piston. Accordingly, the axial drive coils must be energized sequentially as the piston reciprocates, and suitable commutation is required therefor.

Correspondingly, the rotary drive coil 30b is wound axially around the housing for magnetically cooperating with the magnetic poles of the magnet strips 30a for producing magnetic torque for rotating or spinning the piston during operation.

In the preferred embodiment, each of the magnet strips 30a includes radially opposite magnetic north and south poles alternating circumferentially around the piston. The magnetic field emanating from the magnet strips has a radial component that varies sinusoidally circumferentially from pole to pole. This radial magnetic field interacts with electrical current in the axially extending legs of the rotary drive coil 30b to produce torque on the magnet strips. The strength of the radial field is very high and produces high torque with little current in the rotary drive coil and with low losses.

Since the direction of electrical current in the individual axial legs of the rotary drive coil 30b must be opposite over the north and south magnetic poles that torque therefrom is additive, commutation of the rotary drive coil is also required.

Axial commutation of the axial drive coils 26a may be effected in any suitable manner. For example, an axial position transducer or sensor 32 as shown in FIG. 1 may be mounted in the housing 20 adjacent the piston 24 for measuring axial position thereof. The axial sensor is operatively joined to the controller 16 which is configured for sequentially energizing the six axial drive coils 26a in corresponding pairs as the two magnet rings 26b are axially translated therebelow. The axial sensor 32 may measure the axial position of the piston in any conventional manner, such as ultrasonically.

In accordance with another feature of the present invention, the commutating means further comprise a rotary encoder 34 suitably mounted inside the housing outboard of the magnet strips 30a for sensing or measuring change in magnetic field therefrom as the piston rotates or spins.

As shown in FIG. 1, the rotary encoder 34 is preferably mounted axially centrally between opposite axial ends of the rotary drive coil 30b. The magnet strips 30a are sized in axial length to maintain continuous magnetic cooperation with the encoder as the piston oscillates in the housing over its full stroke.

In the preferred embodiment illustrated in FIG. 2, the magnet strips 30a have a relatively small pole pitch A for effecting a tangential magnetic field, illustrated in phantom in FIG. 2, radially inboard of the outer core 26c. The rotary encoder 34 preferably comprises a conventional Hall sensor specifically configured in accordance with another feature of the present invention for measuring primarily only the tangential magnetic field from the magnet strips.

Since the north and south poles illustrated in FIG. 2 reverse between adjacent magnet strips, the radial component of the magnetic field emanating from the strips varies sinusoidally. A complete sine wave of magnetic field thusly extends over the circumferential distance from center to center of two north poles or south poles representing the pole pitch A. Accordingly, the pole pitch A is measured between three circumferentially alternate poles such as N-S-N.

The magnet strips 30a illustrated in FIG. 2 are spaced radially inwardly from the outer core 26c to define a radial offset B therebetween. Preferably, half the pole pitch (A/2) is less than the offset B to uncouple the magnet strips 30a from the outer core 26c. By keeping the pole pitch relatively small in this manner, the magnetic field from the poles is primarily contained in the axial drive coils 26a, and little if any of this field is carried into the outer iron core 26c for minimizing flux therein and size thereof.

Since corresponding drive coils of the linear motor and rotary motor are generally orthogonal to each other, magnetic coupling therebetween is minimal, and pump control is simplified. Furthermore, isolation of the rotary encoder to measure magnetic field from the magnet strips alone is also desired for enhancing control of the pump.

As shown in more detail in FIG. 2, the Hall effect rotary encoder 34 is positioned at the housing bore 20a to measure primarily only the tangential magnetic field emanating from the magnet strips 30a. The preferred small pitch of the magnet strips ensures that the tangential component of the magnetic field, as opposed to its radial component, is detected by the encoder 34.

The tangential magnetic field varies accurately as a sine wave between poles so that a sinusoidal signal is obtained with rotation angle of the piston having a period corresponding with the pole pitch A. By positioning the rotary encoder 34 at the center of the piston stroke as illustrated in FIG. 1, it continuously monitors the tangential field between circumferentially adjacent magnet strips over their full axial extent as the piston axially reciprocates and circumferentially rotates. A continuous and strong encoder signal is thusly provided to the controller for commutating the rotary drive coil 30b.

In the preferred embodiment illustrated in FIG. 2, a pair of the rotary encoder Hall sensors 34 are provided, and are circumferentially offset from each other by a quarter-pitch of the magnet strips. Since the field strength from these strips is maximum at the junction between adjacent poles and is zero at the center of each pole, a cosine signal may be obtained by spacing the second Hall sensor a quarter-pitch away from the first sensor which produces a sine signal. The sine and cosine signals from the two sensors may be obtained by suitably positioning the two sensors circumferentially offset from each other with an effective quarter-pitch offset at one or more of the magnet strips as desired since the magnetic fields therefrom are repetitive.

The Hall sensors are preferred because they provide a highly linear output signal accurately reflecting the variation in magnetic field strength. By positioning the two sensors for obtaining sine and cosine signals, the encoder count is easily subdivided to any desired angular accuracy.

The rotary drive coil 30b illustrated in FIG. 2 includes a plurality of circumferentially adjacent, axially extending legs. Preferably, eight independent rotary drive coil circuits are provided, each with an adjoining leg-pair per pole pitch. These axial legs are provided in multiple, independent adjacent circuits for effecting rotary commutation.

In a preferred embodiment, thirty six magnet strips 30a are preferred which effect eighteen maximum or peak magnetic fields around the circumference of the piston. The use of the two Hall sensors 34 permits electrical division of the eighteen magnetic peaks in multiples or factors of two. By selecting a factor of sixteen (the number of legs per pole pitch) times the eighteen magnetic peaks, two hundred and eighty-eight (288) rotary divisions may be used.

The advantage in measuring only the tangential component of the magnetic field from the magnet strips is that no change in output of the Hall sensors will occur as the magnet rings 26b of the linear motor approach the Hall sensors at the opposite ends of the piston stroke. Since the magnetic field from the magnet rings 26b are directed radially with an axial leakage component, neither radial nor axial component thereof affects the Hall sensors which are configured to sense the tangential magnetic field which is orthogonal to the radial and axial fields of the magnet rings 26b. Accordingly, the rotary encoder maintains its accuracy even closely adjacent to the magnet rings 26b over the entire axial stroke of the piston.

The small pitch of the magnet strips 30a significantly reduces radial leakage of the magnetic field thereof into the outer iron core 26c for correspondingly reducing any radial instability force on the piston as compared to the magnetic fields emanating from the magnet rings 26b. Optimum rotary torque is obtained with a large number of magnet strips 30a, such as thirty-six (36) in the preferred embodiment. Correspondingly, the small pole pitch effected by the large number of magnet strips ensures that the magnetic field from the strips is contained primarily only between the strips and the outer core 26c.

Furthermore, the magnet strips 30a configured in this manner provide little if any adverse effect on the radial component of the magnetic field from the magnet rings 26b. This is important for maintaining the desired linearity of the current-to-force response of the linear motor, and preserves the magnitude of the force constant therefor.

Radial flux leakage from the magnet strips 30a into the outer iron core 26c is relatively small and is orthogonal to the axial flux therein from the magnet rings 26b. The cross section of the outer iron core 26c need not be increased to accommodate radial flux leakage therein, and thusly the weight attributable to the outer core may be minimized.

Accordingly, the rotary motor 30 is integrated into the pump 10 illustrated in FIG. 1 in combination with the linear motor 26, yet remains magnetically uncoupled therefrom. The linear and rotary motors may thusly be independently optimized for operation and performance without adversely affecting each other. Power requirements for the two motors may be substantially reduced as indicated above for increasing the overall efficiency of the linear pump.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims in which I claim:

1. A pump for pumping a fluid comprising:
    a housing having a coaxial bore disposed in flow communication between a housing inlet and a housing outlet axially spaced apart at opposite ends thereof;

a piston disposed coaxially in said housing bore for axial translation therein, and having a coaxial bore disposed in flow communication between a piston inlet and a piston outlet axially spaced apart at opposite ends thereof;

a check valve disposed in said piston for controlling flow of said fluid therethrough;

a linear motor operatively joined in said housing and piston for axially oscillating said piston in said housing to pump said fluid in unidirection flow therethrough;

a rotary motor for spinning said piston, and including a plurality of circumferentially adjoining magnet strips mounted around said piston centrally between said opposite ends thereof, and a magnetically cooperating rotary drive coil mounted inside said housing around said housing bore; and said rotary motor being distinct from said linear motor and magnetically uncoupled therefrom.

2. A pump according to claim 1 wherein said linear motor comprises:

a plurality of axially adjoining axial drive coils mounted inside said housing around said rotary drive coil; and a pair of axially spaced apart magnet rings mounted inside said piston at opposite ends of said magnet strips for magnetically cooperating with said axial drive coils to axially oscillate said piston.

3. A pump according to claim 2 further comprising means for commutating said axial and rotary drive coils.

4. A pump according to claim 3 wherein said commutating means comprise a rotary encoder mounted in said housing outboard of said magnet strips for sensing change in magnetic field therefrom as said piston spins.

5. A pump according to claim 4 wherein:

said rotary encoder is mounted centrally between opposite ends of said rotary drive coil; and said magnet strips are sized in length to maintain continuous magnetic cooperation with said encoder as said piston oscillates in said housing.

6. A pump according to claim 4 wherein:

each of said magnet strips includes radially opposite poles alternating circumferentially around said piston, with a pole pitch defined between three circumferentially alternate poles; and said magnet strips are spaced radially inwardly from said linear motor, with said pole pitch selected to minimize flux from said strips in an outer core of said linear motor.

7. A pump according to claim 4 wherein:

said housing further includes an iron outer core surrounding said axial drive coils; and said piston further includes an iron inner core disposed inboard of said magnet strips and magnet rings.

8. A pump according to claim 4 wherein:

said magnet strips have a pole pitch for effecting a tangential magnetic field; and said rotary encoder comprises a Hall sensor configured for measuring primarily only said tangential magnetic field from said magnet strips.

9. A pump according to claim 8 further comprising a pair of said Hall sensors circumferentially offset from each other by a quarter-pitch of said magnet strips.

10. A pump according to claim 9 wherein said rotary drive coil includes a plurality of circumferentially adjoining legs in multiple independent circuits.

11. A pump for pumping a fluid comprising:

a housing having a coaxial bore disposed in flow communication between a housing inlet and a housing outlet axially spaced apart at opposite ends thereof;

a piston disposed coaxially in said housing bore for axial translation therein, and having a coaxial bore disposed in flow communication between a piston inlet and a piston outlet axially spaced apart at opposite ends thereof;

a check valve disposed in said piston for controlling flow of said fluid therethrough;

a rotary motor for spinning said piston, and including a plurality of circumferentially adjoining magnet strips mounted around said piston centrally between said opposite ends thereof, and a magnetically cooperating rotary drive coil mounted inside said housing around said housing bore; and a linear motor operatively joined in said housing and piston for axially oscillating said piston in said housing to pump said fluid in unidirection flow therethrough, and comprising:

a plurality of axially adjoining axial drive coils mounted inside said housing 20 around said rotary drive coil; and a pair of axially spaced apart magnet rings mounted inside said piston at opposite ends of said magnet strips for magnetically cooperating with said axial drive coils to axially oscillate said piston.

12. A pump according to claim 11 further comprising means for commutating said axial and rotary drive coils including a rotary encoder mounted in said housing outboard of said magnet strips for sensing change in magnetic field therefrom as said piston spins.

13. A pump according to claim 12 wherein said rotary encoder comprises a Hall sensor configured for measuring primarily only tangential magnetic field from said magnet strips.

14. A pump according to claim 13 wherein:

said Hall sensor is mounted centrally between opposite ends of said rotary drive coil; and said magnet strips are sized in length to maintain continuous magnetic cooperation with said encoder as said piston oscillates in said housing.

15. A pump according to claim 14 further comprising a pair of said Hall sensors circumferentially offset from each other by a quarter-pitch of said magnet strips.

16. A pump according to claim 15 wherein:

each of said magnet strips includes radially opposite poles alternating circumferentially around said piston, with a pole pitch between three circumferentially alternate poles; and said magnet strips are spaced radially inwardly from said linear motor, with said pole pitch selected to minimize flux from said strips in an outer core of said linear motor.

17. A pump according to claim 16 wherein said commutating means further comprise an axial position sensor mounted in said housing adjacent said piston for measuring axial position thereof.

* * * * *